United States Patent [19]

Kishimoto et al.

[11] Patent Number: 5,360,894
[45] Date of Patent: Nov. 1, 1994

[54] C/EBP2 GENE AND RECOMBINANT C/EBP2

[75] Inventors: Tadamitsu Kishimoto, Tondabayashi; Toshio Hirano, Ibaragi; Shizuo Akira, Minoo; Hiroshi Isshiki, Osaka; Osamu Tanabe, Hiroshima; Shigemi Kinoshita, Ibaragi; Takuya Shimamoto, Minoo, all of Japan

[73] Assignee: Tadamitsu Kishimoto, Osaka, Japan

[21] Appl. No.: 12,735

[22] Filed: Feb. 3, 1993

Related U.S. Application Data

[62] Division of Ser. No. 601,094, Oct. 22, 1990.

[30] Foreign Application Priority Data

Dec. 25, 1989 [JP] Japan .................... 336868

[51] Int. Cl.⁵ .............. C07K 3/00; C12P 21/02; C12P 19/34; C12N 15/00
[52] U.S. Cl. .................... 530/350; 530/300; 435/69.1; 435/252.33; 435/240.1; 435/235.1; 435/320.1; 435/172.3; 935/34

[58] Field of Search ............... 530/350, 300; 435/69.1, 435/252.33, 172.3, 255, 256, 252.33, 320.1, 240.1, 235.1, 91; 935/34

[56] References Cited

PUBLICATIONS

Land Schulz et al. Genes & Development vol. 2 pp. 786–800 (1988).

Primary Examiner—Joan Ellis
Attorney, Agent, or Firm—Sughrue, Mion, Zinn, Macpeak & Seas

[57] ABSTRACT

This invention relates to a gene which codes for the IL-6 gene expression inducing nuclear factor C/EBP2 capable of binding sequence-specifically to the palindrome structure SEQ ID NO:2 located in the transcriptional regulatory region of the IL-6 gene; an expression plasmid with the C/EBP2 gene incorporated therein; an transformant harboring the expression plasmid; a recombinant C/EBP2 obtained by expressing the C/EBP2 gene; and a method of producing the recombinant C/EBP2.

2 Claims, 5 Drawing Sheets

↓ Cla I
↓ CIP
↓ Linker-ligation

FIG. 5

| Plasmid | Oligonucleotide linker |
|---------|------------------------|
| ptrp 690 | 5'-CGTATTACGCGTAAGGAAATCCAT-3'<br>3'-ATAATGCGCATTCCTTTAGGTAGC-5' |
| ptrp 691 | 5'-CGAATCTAGATGCACAGGAGACTTTCTAT-3'<br>3'-TTAGATCTACGTGTCCTCTGAAAGATAGC-5' |
| ptrp 692 | 5'-CGTCGACGCGTTGAGGCTTGCGTTTAT-3'<br>3'-AGCTGCGCAACTCCGAACGCAAATAGC-5' |
| ptrp 693 | 5'-CGAATACGCGTCATGACAGGAGTAAAAT-3'<br>3'-TTATGCGCAGTACTGTCCTCATTTTAGC-5' |
| ptrp 694 | 5'-CGTATGTCTAGAATATGGAGGAAATTAT-3'<br>3'-ATACAGATCTTATACCTCCTTTAATAGC-5' |
| ptrp 695 | 5'-CGTTTAACGCGTTAAAGGAAGGATCAT-3'<br>3'-AAATTGCGCAATTTCCTTCCTAGTAGC-5' |
| ptrp 696 | 5'-CGAAATCTAGATGCAAAGGAGATTTAT-3'<br>3'-TTTAGATCTACGTTTCCTCTAAATAGC-5' |
| ptrp 697 | 5'-CGTCGACGCGTTGAGGCTTAAATTTAT-3'<br>3'-AGCTGCGCAACTCCGAATTTAAATAGC-5' |
| ptrp 698 | 5'-CGAATACGCGTCATTATAGGATTAAT-3'<br>3'-TTATGCGCAGTAATATCCTAATTAGC-5' |
| ptrp 699 | 5'-CGTATGTCTGAGAATTTGGAGGTTTAAAT-3'<br>3'-ATACAGACTCTTAAACCTCCAAATTTAGC-5' |

SEQUENCE LISTING ( 1 ) GENERAL INFORMATION:

( i i i ) NUMBER OF SEQUENCES: 34

( 2 ) INFORMATION FOR SEQ ID NO:1:

( i ) SEQUENCE CHARACTERISTICS:
        ( A ) LENGTH: 1914 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 281..1316
        ( D ) OTHER INFORMATION:

( x i ) SEQUENCE DESCRIPTION: SEQ ID NO:1:

```
GTCCTTCGCG  TCCCGGCGGC  GCGGCGGAGG  GGCCGGCGTG  ACGCAGCGGT      50

TGCTACGGGC  CGCCCTTATA  AATAACCGGG  CTCAGGAGAA  ACTTTAGCGA     100

GTCAGAGCCG  CGCACGGACT  GGGAAGGGGA  CCCACCCGAG  GGTCCAGCCA     150

CCAGCCCCCT  CACTAATAGC  GGCCACCCCG  GCAGCGGCGG  CAGCAGCAGC     200

AGCGACGCAG  CGGCGACAGC  TCAGAGCAGG  GAGGCCGCGC  ACCTGCGGGC     250

CGGCCGGAGC  GGGCAGCCCC  AGGCCCCCTC  ATGCAACGCC  TGGTGGCCTG     300

GGACCCAGCA  TGTCTCCCCC  TGCCGCCGCC  GCCGCCTGCC  TTTAAATCCA     350

TGGAAGTGGC  CAACTTCTAC  TACGAGGCGG  ACTGCTTGGC  TGCTGCGTAC     400

GGCGGCAAGG  CGGCCCCCGC  GGCGCCCCCC  GCGGCCAGAC  CCGGGCCGCG     450

CCCCCCCGCC  GGCGAGCTGG  GCAGCATCGG  CGACCACGAG  CGCGCCATCG     500

ACTTCAGCCC  GTACCTGGAG  CCGCTGGGCG  CGCCGCAGGC  CCCGGCGCCC     550

GCCACGGCCA  CGGACACCTT  CGAGGCGGCT  CCGCCCGCGC  CGCCCCCGC      600

GCCCGCCTCC  TCCGGGCAGC  ACCACGACTT  CCTCTCCGAC  CTCTTCTCCG     650

ACGACTACGG  GGGCAAGAAC  TGCAAGAAGC  CGGCCGAGTA  CGGCTACGTG     700

AGCCTGGGGC  GCCTGGGGGC  TGCCAAGGGC  GCGCTGCACC  CCGGCTGCTT     750

CGCGCCCCTG  CACCCACCGC  CCCCGCCGCC  GCCGCCGCCC  GCCGAGCTCA     800
```

| | | | | | |
|---|---|---|---|---|---|
| AGGCGGAGCC | GGGCTTCGAG | CCCGCGGACT | GCAAGCGGAA | GGAGGAGGCC | 850 |
| GGGGCGCCGG | GCGGCGGCGC | AGGCATGGCG | GCGGGCTTCC | CGTACGCGCT | 900 |
| GCGCGCTTAC | CTCGGCTACC | AGGCGGTGCC | GAGCGGCAGC | AGCGGGAGCC | 950 |
| TCTCCACGTC | CTCCTCGTCC | AGCCCGCCCG | GCACGCCGAG | CCCCGCTGAC | 1000 |
| GCCAAGGCCC | CCCCGACCGC | CTGCTACGCG | GGGGCCGGGC | CGGCGCCCTC | 1050 |
| GCAGGTCAAG | AGCAAGGCCA | AGAAGACCGT | GGACAAGCAC | AGCGACGAGT | 1100 |
| ACAAGATCCG | GCGCGAGCGC | AACAACATCG | CCGTGCGCAA | GAGCCGCGAC | 1150 |
| AAGGCCAAGA | TGCGCAACCT | GGAGACGCAG | CACAAGGTCC | TGGAGCTCAC | 1200 |
| GGCCGAGAAC | GAGCGGCTGC | AGAAGAAGGT | GGAGCAGCTG | TCGCGCGAGC | 1250 |
| TCAGCACCCT | GCGGAACTTG | TTCAAGCAGC | TGCCCGAGCC | CCTGCTCGCC | 1300 |
| TCCTCCGGCC | ACTGCTAGCG | CGGCCCCGC | GGCGTCCCCC | TGGGGCCGGC | 1350 |
| CGGGGCTGAG | ACTCCGGGGA | GCGCCCGCGC | CCGCGCCCTC | GCCCCCNCCC | 1400 |
| CCNNNNCCGC | AAAACTTTGG | CACTGGGGCA | CTTGGCAGCN | GGGGAGCCCG | 1450 |
| TCGGTAATTT | TAATATTTTA | TTATATATAT | ATATCTATAT | TTTGCCAACC | 1500 |
| AACCGTACAT | GCAGATGGCT | CCCGCCCGTG | GTGTATAAAG | AAGAAATGTC | 1550 |
| TATGTGTACA | GATGAATGAT | AAACTCTCTG | CTCTCCCTCT | GCCCCTCTCC | 1600 |
| AGGCCCGGCG | GGCGGGGCCG | GTTTCGAAGT | TGATGCAATC | GGTTTAAACA | 1650 |
| TGGCTGAACG | CGTGTGTACA | CGGGACTGAC | GCAACCCACG | TGTAACTGTC | 1700 |
| AGCCGGGCCC | TGAGTAATCG | CTTAAAGATG | TTCTAGGGCT | TGTTGCTGTT | 1750 |
| GATGTTTTGT | TTTGTTTTGT | TTTTGGTGT | TTTTTCTAT | TATAAAAAAT | 1800 |
| AATCTATTTC | TATGAGAAAA | GACGCGTCTG | TATATTTTGG | GAATCTTTTC | 1850 |
| CGTTTCAAGC | AATTAAGAAC | ACTTTAATA | AACTTTTTTT | TGAGAATGGT | 1900 |
| TAAAAAAAA | AAAAA | | | | 1914 |

( 2 ) INFORMATION FOR SEQ ID NO:2:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

| | |
|---|---|
| ACATTGCACA ATCT | 14 |

( 2 ) INFORMATION FOR SEQ ID NO:3:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

| | |
|---|---|
| GATCGGACGT CACATTGCAC AATCTTAATA AT | 32 |

( 2 ) INFORMATION FOR SEQ ID NO:4:

( i ) SEQUENCE CHARACTERISTICS:
        ( A ) LENGTH: 32 base pairs
        ( B ) TYPE: nucleic acid ( C ) STRANDEDNESS: single
( D ) TOPOLOGY: linear ( i i ) MOLECULE TYPE: cDNA ( x i ) SEQUENCE DESCRIPTION: SEQ ID NO:4:

GATCATTATT AAGATTGTGC AATGTGACGT CC 32

( 2 ) INFORMATION FOR SEQ ID NO:5:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

AGATTGCACA ATCTGATCAG ATTGCACAAT CTGATCGATT CGACAATCT 49

( 2 ) INFORMATION FOR SEQ ID NO:6:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..45
        ( D ) OTHER INFORMATION:

( x i ) SEQUENCE DESCRIPTION: SEQ ID NO:6:

```
TCC ACG TCC TCC TCG TCC AGC CCG CCC GGC ACG CCG AGC CCC  42
Ser Thr Ser Ser Ser Ser Ser Pro Pro Gly Thr Pro Ser Pro
1               5                   10              14

GCT                                                      45
Ala
15
```

( 2 ) INFORMATION FOR SEQ ID NO:7:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..51
        ( D ) OTHER INFORMATION:

( x i ) SEQUENCE DESCRIPTION: SEQ ID NO:7:

```
AGC AAG GCC AAG AAG ACC GTG GAC AAG CAC AGC GAC GAG TAC  42
Ser Lys Ala Lys Lys Thr Val Asp Lys His Ser Asp Glu Tyr
1               5                   10              14

AAG ATC CGG                                              51
Lys Ile Arg
15      17
```

( 2 ) INFORMATION FOR SEQ ID NO:8:

( i ) SEQUENCE CHARACTERISTICS:
        ( A ) LENGTH: 24 base pairs (B) TYPE: nucleic acid
(C) STRANDEDNESS: double
(D) TOPOLOGY: linear (ii) MOLECULE TYPE: cDNA (xi) SEQUENCE DESCRIPTION: SEQ ID NO:8:

CGTATTACGC GTAAGGAAAT CCAT    24

(2) INFORMATION FOR SEQ ID NO:9:

(i) SEQUENCE CHARACTERISTICS:
(A) LENGTH: 24 base pairs
(B) TYPE: nucleic acid
(C) STRANDEDNESS: double
(D) TOPOLOGY: linear (ii) MOLECULE TYPE: cDNA (xi) SEQUENCE DESCRIPTION: SEQ ID NO:9:

CGATGGATTT CCTTACGCGT AATA    24

(2) INFORMATION FOR SEQ ID NO:10:

(i) SEQUENCE CHARACTERISTICS:
(A) LENGTH: 29 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:10:

CGAATCTAGA TGCACAGGAG ACTTTCTAT    29

(2) INFORMATION FOR SEQ ID NO:11:

(i) SEQUENCE CHARACTERISTICS:
(A) LENGTH: 29 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:11:

CGATAGAAAG TCTCCTGTGC ATCTAGATT    29

(2) INFORMATION FOR SEQ ID NO:12:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:12:

CGTCGACGCG TTGAGGCTTG CGTTTAT    27

(2) INFORMATION FOR SEQ ID NO:13:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:13:

CGATAAACGC AAGCCTCAAC GCGTCGA 27

( 2 ) INFORMATION FOR SEQ ID NO:14:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:14:

CGAATACGCG TCATGACAGG AGTAAAAT 28

( 2 ) INFORMATION FOR SEQ ID NO:15:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:15:

CGATTTACT CCTGTCATGA CGCGTATT 28

( 2 ) INFORMATION FOR SEQ ID NO:16:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:16:

CGTATGTCTA GAATATGGAG GAAATTAT 28

( 2 ) INFORMATION FOR SEQ ID NO:17:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:17:

CGATAATTTC CTCCATATTC TAGACATA 28

( 2 ) INFORMATION FOR SEQ ID NO:18:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:18:

CGTTTAACGC GTTAAAGGAA GGATCAT 27

( 2 ) INFORMATION FOR SEQ ID NO:19:

( i ) SEQUENCE CHARACTERISTICS:

(A) LENGTH: 27 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:19:

CGATGATCCT TCCTTTAACG CGTTAAA 27

(2) INFORMATION FOR SEQ ID NO:20:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:20:

CGAAATCTAG ATGCAAAGGA GATTTAT 27

(2) INFORMATION FOR SEQ ID NO:21:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:21:

CGATAAATCT CCTTTGCATC TAGATTT 27

(2) INFORMATION FOR SEQ ID NO:22:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:22:

CGTCGACGCG TTGAGGCTTA AATTTAT 27

(2) INFORMATION FOR SEQ ID NO:23:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:23:

CGATAAATTT AAGCCTCAAC GCGTCGA 27

(2) INFORMATION FOR SEQ ID NO:24:

(i) SEQUENCE CHARACTERISTICS:
(A) LENGTH: 26 base pairs
(B) TYPE: nucleic acid
(C) STRANDEDNESS: single
(D) TOPOLOGY: linear (ii) MOLECULE TYPE: cDNA ( x i ) SEQUENCE DESCRIPTION: SEQ ID NO:24:

CGAATACGCG TCATTATAGG ATTAAT                26

( 2 ) INFORMATION FOR SEQ ID NO:25:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:25:

CGATTAATCC TATAATGACG CGTATT                26

( 2 ) INFORMATION FOR SEQ ID NO:26:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:26:

CGTATGTCTG AGAATTTGGA GGTTTAAAT             29

( 2 ) INFORMATION FOR SEQ ID NO:27:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:27:

CGATTTAAAC CTCCAAATTC TCAGACATA             29

( 2 ) INFORMATION FOR SEQ ID NO:28:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:28:

AACTAGTACG CAT                              13

( 2 ) INFORMATION FOR SEQ ID NO:29:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:29:

CGATGCGTAC TAGTT                            15

( 2 ) INFORMATION FOR SEQ ID NO:30:

( i ) SEQUENCE CHARACTERISTICS:
    ( A ) LENGTH: 1035 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: CDS
    ( B ) LOCATION: 1..1035
    ( D ) OTHER INFORMATION:

( x i ) SEQUENCE DESCRIPTION: SEQ ID NO:30:

```
ATG CAA CGC CTG GTG GCC TGG GAC CCA GCA TGT CTC CCC CTG      42
Met Gln Arg Leu Val Ala Trp Asp Pro Ala Cys Leu Pro Leu
 1               5                  10

CCG CCG CCG CCG CCT GCC TTT AAA TCC ATG GAA GTG GCC AAC      84
Pro Pro Pro Pro Pro Ala Phe Lys Ser Met Glu Val Ala Asn
15                  20                  25

TTC TAC TAC GAG GCG GAC TGC TTG GCT GCT GCG TAC GGC GGC     126
Phe Tyr Tyr Glu Ala Asp Cys Leu Ala Ala Ala Tyr Gly Gly
         30                  35                  40

AAG GCG GCC CCC GCG GCG CCC CCC GCG GCC AGA CCC GGG CCG     168
Lys Ala Ala Pro Ala Ala Pro Pro Ala Ala Arg Pro Gly Pro
                 45                  50                  55

CGC CCC CCC GCC GGC GAG CTG GGC AGC ATC GGC GAC CAC GAG     210
Arg Pro Pro Ala Gly Glu Leu Gly Ser Ile Gly Asp His Glu
             60                  65                  70

CGC GCC ATC GAC TTC AGC CCG TAC CTG GAG CCG CTG GGC GCG     252
Arg Ala Ile Asp Phe Ser Pro Tyr Leu Glu Pro Leu Gly Ala
                 75                  80

CCG CAG GCC CCG GCG CCC GCC ACG GCC ACG GAC ACC TTC GAG     294
Pro Gln Ala Pro Ala Pro Ala Thr Ala Thr Asp Thr Phe Glu
85                  90                  95

GCG GCT CCG CCC GCG CCC GCC CCC GCG CCC GCC TCC TCC GGG     336
Ala Ala Pro Pro Ala Pro Ala Pro Ala Pro Ala Ser Ser Gly
             100                 105                 110

CAG CAC CAC GAC TTC CTC TCC GAC CTC TTC TCC GAC GAC TAC     378
Gln His His Asp Phe Leu Ser Asp Leu Phe Ser Asp Asp Tyr
             115                 120                 125

GGG GGC AAG AAC TGC AAG AAG CCG GCC GAG TAC GGC TAC GTG     420
Gly Gly Lys Asn Cys Lys Lys Pro Ala Glu Tyr Gly Tyr Val
                 130                 135                 140

AGC CTG GGG CGC CTG GGG GCT GCC AAG GGC GCG CTG CAC CCC     462
Ser Leu Gly Arg Leu Gly Ala Ala Lys Gly Ala Leu His Pro
                 145                 150

GGC TGC TTC GCG CCC CTG CAC CCA CCG CCC CCG CCG CCG        504
Gly Cys Phe Ala Pro Leu His Pro Pro Pro Pro Pro Pro
155                 160                 165

CCG CCC GCC GAG CTC AAG GCG GAG CCG GGC TTC GAG CCC GCG     546
Pro Pro Ala Glu Leu Lys Ala Glu Pro Gly Phe Glu Pro Ala
    170                 175                 180

GAC TGC AAG CGG AAG GAG GAG GCC GGG GCG CCG GGC GGC GGC     588
Asp Cys Lys Arg Lys Glu Glu Ala Gly Ala Pro Gly Gly Gly
            185                 190                 195

GCA GGC ATG GCG GCG GGC TTC CCG TAC GCG CTG CGC GCT TAC     630
Ala Gly Met Ala Ala Gly Phe Pro Tyr Ala Leu Arg Ala Tyr
                200                 205                 210

CTC GGC TAC CAG GCG GTG CCG AGC GGC AGC AGC GGG AGC CTC     672
Leu Gly Tyr Gln Ala Val Pro Ser Gly Ser Ser Gly Ser Leu
                    215                 220

TCC ACG TCC TCC TCG TCC AGC CCG CCC GGC ACG CCG AGC CCC     714
Ser Thr Ser Ser Ser Ser Ser Pro Pro Gly Thr Pro Ser Pro
225                 230                 235
```

```
GCT GAC GCC AAG GCC CCC CCG ACC GCC TGC TAC GCG GGG GCC    756
Ala Asp Ala Lys Ala Pro Pro Thr Ala Cys Tyr Ala Gly Ala
    240         245                     250

GGG CCG GCG CCC TCG CAG GTC AAG AGC AAG GCC AAG AAG ACC    798
Gly Pro Ala Pro Ser Gln Val Lys Ser Lys Ala Lys Lys Thr
        255                 260                 265

GTG GAC AAG CAC AGC GAC GAG TAC AAG ATC CGG CGC GAG CGC    840
Val Asp Lys His Ser Asp Glu Tyr Lys Ile Arg Arg Glu Arg
            270                 275                 280

AAC AAC ATC GCC GTG CGC AAG AGC CGC GAC AAG GCC AAG ATG    882
Asn Asn Ile Ala Val Arg Lys Ser Arg Asp Lys Ala Lys Met
                285                 290

CGC AAC CTG GAG ACG CAG CAC AAG GTC CTG GAG CTC ACG GCC    924
Arg Asn Leu Glu Thr Gln His Lys Val Leu Glu Leu Thr Ala
295                 300                 305

GAG AAC GAG CGG CTG CAG AAG AAG GTG GAG CAG CTG TCG CGC    966
Glu Asn Glu Arg Leu Gln Lys Lys Val Glu Gln Leu Ser Arg
        310                 315                 320

GAG CTC AGC ACC CTG CGG AAC TTG TTC AAG CAG CTG CCC       1008
Glu Leu Ser Thr Leu Arg Asn Leu Phe Lys Gln Leu Pro
            325                 330                 335

GAG CCC CTG CTC GCC TCC TCC GGC CAC TGC                   1035
Glu Pro Leu Leu Ala Ser Ser Gly His Cys
            340                 345
```

( 2 ) INFORMATION FOR SEQ ID NO:31:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: protein ( x i ) SEQUENCE DESCRIPTION: SEQ ID NO:31:

```
Ser Thr Ser Ser Ser Ser Ser Pro Pro Gly Thr Pro Ser Pro Ala
1               5                   10                  15
```

( 2 ) INFORMATION FOR SEQ ID NO:32:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: protein ( x i ) SEQUENCE DESCRIPTION: SEQ ID NO:32:

```
Ser Lys Ala Lys Lys Thr Val Asp Lys His Ser Asp Glu Tyr
1               5                   10                  14

Lys Ile Arg
15      17
```

( 2 ) INFORMATION FOR SEQ ID NO:33:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:33:

CGATAATGCA ACGTTTAGTA GCATGGGATC CAGCATG           37

( 2 ) INFORMATION FOR SEQ ID NO:34:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:34:

CTGGATCCCA TGCTACTAAA CGTTGCATTA T        31

C/EBP2 GENE AND RECOMBINANT C/EBP2

This is a divisional of application Ser. No. 07/601,094 filed Oct. 22, 1990.

FIELD OF THE INVENTION

This invention relates to a gene for a nuclear factor capable of inducing the expression of the interleukin-6 (IL-6) gene. More particularly, it relates to a gene coding for a nuclear factor capable of binding sequence-specifically to the palindrome structure ACATTGCACAATCT occurring in the transcriptional regulatory region of the IL-6 gene to induce the expression of IL-6, which is useful as a drug. Furthermore, it relates to the above-mentioned nuclear factor produced by using the gene mentioned above, namely the recombinant nuclear factor C/EBP2. Said nuclear factory can induce IL-6 production in vivo to enhance hematopoiesis, for instance.

BACKGROUND ART

IL-6 is an important physiologically active factor which is involved not only in the immune system but also in the proliferation and differentiation of hematopoietic progenitor cells, induction of acutephase proteins and differentiation of nerve cells. The biological activities of said IL-6 may be classified roughly into three types, namely (1) induction of cell differentiation or induction of the expression of certain genes, (2) induction of cell proliferation and (3) inhibition of cell proliferation. It has been shown that IL-6 produce quite different biological activities against different targent cells [Hirano, T. and Kishimoto, T., Jikken Igaku, 7 (1), 11–12 (1989)].

On the other hand, it is known that IL-6 is produced to an abnormal extent in patients with certain autoimmune diseases or cancer, among others [Kishimoto, T. and Hirano, T.: Molecular regulation of B lymphocyte response, Ann. Rev. Immunol., 6, 485–512 (1988)].

Analysis of the genes of cells abnormally producing IL-6 in patients with diseases accompanied by abnormal IL-6 production has revealed that the gene coding for IL-6 itself has not undergone any gene mutation or any other changes in its structure. This suggests that the abnormal IL-6 production mentioned above might be induced by occurrence of an abnormality in a nuclear factor which controls the transcription of the IL-6 gene.

Meanwhile it is known that the production of IL-6 is induced by stimulation from interleukin-1 (IL-1) [Kishimoto, T. and Hirano, T.: Molecular regulation of B lymphocyte response, Ann. Rev. Immunol., 6, 485–512 (1988)].

The present inventors made intensive investigations in the belief that a nuclear factor capable of directing acting on the IL-1-induced IL-6 gene expression must be found in glioblastoma cells (tumor cells derived from cerebral glia cells) [SK-MG4; Yasukawa, K, et al., EMBO Journal, 6, 2939–2945 (1987)]and, as a result, found that a region having homology to c-fos SRE [Treisman, R., Cell, 42, 889–902 (1985)]occurs in the 5' upstream region of the IL-6 gene and that there is a nuclear factor capable of sequence-specifically binding to the 14 bp palidrome structure SEQ ID NO:2 occurring in said region homologous to c-fos SRE. Said nuclear factor was first named NF-IL6 (Akira, S. et al., Abstracts of Papers presented at the Annual Meeting of the Japanese Society for Immunology for 1988, page 281). The name of said factor has been changed to C/EBP2.

It is an object of the invention to isolate the gene coding for the nuclear factor (i.e. C/EBP2) capable of sequence-specifically binding to the above-mentioned base sequence SEQ ID NO:2, determine the base sequence of said gene, and produce C/EBP2 by using said gene and the recombinant DNA technology.

SUMMARY OF THE INVENTION

The invention provides a gene coding for the IL-6 gene expression inducing nuclear factor capable of sequence-specifically binding to the palindrome structure SEQ ID NO:2 occurring in the transcriptional regulatory region of the IL-6 gene. (In the present specification, the factor mentioned above is hereinafter referred to as "C/EBP2" and the gene for said factor as "C/EBP2 gene".)

The invention also provides an expression plasmid with the above-mentioned C/EBP2 gene incorporated therein, a microorganism harboring the expression plasmid and a method of producing a recombinant C/EBP2 by cultivating the microorganism as well as the recombinant C/EBP2 produced by said method.

Hereinafter amino acids, peptides, base sequences, nucleic acids and the like are represented by those abbreviations or symbols that are recommended by the IUPAC-IUB Commission on Biochemical Nomenclature or conventionally used in the art. Examples of three-letter and one-letter amino acid designations are shown below:

| Asparagine | Asn (N) | Alanine | Ala (A) |
|---|---|---|---|
| Aspartic acid | Asp (D) | Arginine | Arg (R) |
| Isoleucine | Ile (I) | Glycine | Gly (G) |
| Glutamic acid | Glu (E) | Glutamine | Gln (Q) |
| Cysteine | Cys (C) | Serine | Ser (S) |
| Tryptophan | Trp (W) | Tyrosine | Tyr (Y) |
| Threonine | Thr (T) | Valine | Val (V) |
| Phenylalanine | Phe (F) | Histidine | His (H) |
| Proline | Pro (P) | Methionine | Met (M) |
| Lysine | Lys (K) | Leucine | Leu (L) |

The gene according to the invention codes for the IL-6 gene expression inducing nuclear factor C/EBP2, as mentioned above and contains the genetic information that makes it possible to produce a polypeptide having the amino acid sequence specified herein, namely the recombinant C/EBP2, using genetic engineering techniques. In this respect, said gene can advantageously be used in the production of said recombinant C/EBP2. The present invention also provides such recombinant C/EBP2 which can induce the expression of the IL-6 gene. Therefore application of said recombinant C/EBP2 to a living body can result in IL-6 production in said living body. In this respect, the recombinant C/EBP2 according to the invention is useful, for example, as a hematopoiesis enhancer which induces IL-6 production.

In the specification, the accompanying drawings are referred to, wherein.

Figure 1:
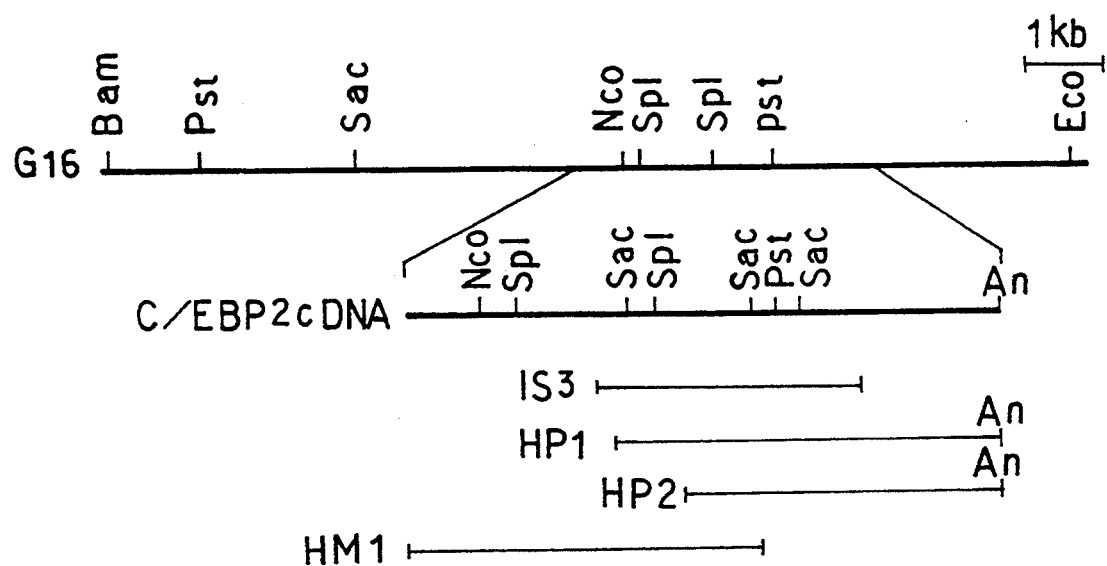
FIG. 1 shows the restriction enzyme maps of IS3, HP1, HP2, HM1, G16 and the C/EBP2 cDNA.

In the figures, Ap ® stands for ampicillin resistance, Tc ® for tetracycline resistance and trp for the tryptophan promoter.

FIG. 5 shows various oligonucleotide linkers for constructing the plasmids ptrp690 to ptrp699.

DETAILED DESCRIPTION OF THE INVENTION

It has already been confirmed by the present inventors that C/EBP2 binds specifically to the specific base sequence SEQ ID NO:2. Said base sequence can be synthesized by a generally known method, as described later therein in a reference example.

The base sequence of the gene according to the invention can be determined and said gene can be produced generally as follows, although specific examples thereof are to be given later herein.

The gene according to the invention can be isolated by the method of Singh et al. [Singh, H. et al., Cell, 52, 415–423 (Feb. 12, 1988)] utilizing the ability of the nuclear factor according to the invention to bind to the specific base sequence mentioned above.

The mRNA required as a template for the synthesis of the cDNA of the gene according to the invention can be isolated from appropriate animal-derived cells, for example human placental cells, human monocytes or human fibroblasts, by a conventional extraction procedure. Thus, for example, for the RNA extraction mentioned above, cells are partly or completely disrupted and solubilized, or lyzed, by the use of a guanidinium thiocyanate solution or an appropriate detergent, such as SDS, NP-40, Triton X100 or deoxycholic acid, or with a homogenizer or by some physical method such as the freeze-thaw method. The chromosomal DNA is then sheared to some extent using a Polytron (Kinematica, Switzerland) or like mixer or a syringe. A nucleic acid fraction is then separated from proteins. Generally used for this extraction procedure are, for example, the phenol-chloroform extraction method and the guanidinium/cesium chloride method [Maniatis, T., Fritsch, E. F. and Sambrook, J., Molecular Cloning—A Laboratory Manual, pages 194–196, Cold Spring Harbor Laboratory, 1982).

To prevent the degradation of RNA with RNase, the above method or procedure can be carried out in the presence of an RNase inhibitor, such as heparin, polyvinyl sulfate, diethyl pyrocarbonate, vanadium complex, bentonite or macaloid.

The isolation and purification of mRNA from the RNA obtained by the above procedure can be effected by an adsorption column method or batchwise method using, for example, oligo-dT-cellulose (Collaborative Research Inc.), poly-U-Sepharose (Pharmacia) or the like.

The thus-obtained purified mRNA, which is usually unstable, is reversely transcribed to give the corresponding, stable complementary DNA (cDNA), which is then inserted to a replicon derived from a microorganism for the amplification of the desired gene. In vitro conversion of the mRNA to the cDNA, i.e. synthesis of the cDNA, can be realized in the following manner, for instance.

Using oligo dT as a primer (which may be a dT-tailed vector primer) and the mRNA as a template, a single-stranded DNA complementary to the mRNA is synthesized in the presence of dNTP (dATP, dGTP, dCTP and dTTP) and a reverse transcriptase. The next step differs as follows depending on whether oligo dT or a dT-tailed vector primer is used.

In the former case, the mRNA used as a template is removed by alkaline hydroysis, and a double-stranded DNA is synthesized from the single-stranded DNA serving as a template, using a reverse transcriptase or DNA polymerase I. Subsequently, both ends of the double-stranded DNA are treated with exonuclease, a suitable linker DNA or a combination of bases amenable to annealing is attached to each end, and the resulting DNA is inserted into a suitable vector, such as a EK-type plasmid vector or λgt phage vector.

In the latter case, the mRNA used as a template, an opened plasmid with a combination of bases, which is amenable to annealing, attached to each end, as in the former case, and a linker DNA (frequently used as such is a DNA fragment having a region which can be autonomously replicated in an animal cell and a transcriptional promoter region of mRNA) are annealed into a circular form. The mRNA is thereafter replaced by the corresponding DNA strand in the presence of dNTP and also in the presence of both RNase H and DNA polymerase I to obtain a recombinant plasmid containing cDNA.

The DNA thus obtained is then introduced into a suitable host, such as *Escherichia coli, Bacillus subtilis* or *Saccharomyces cerevisiae*, for transformation. The DNA can be introduced into the host for transformation thereof, using a usual method, for example, by collecting cells preferably in the logarithmic growth phase, treating the cells with $CaCl_2$ to make them ready for spontaneous uptake of the DNA. This method can be practiced in the presence of $MgCl_2$ or RbCl as is generally known to achieve an improved transformation efficiency. The host cells can be converted to spheroplasts or protoplasts before transformation. When the λ phage, which is generally used as a phage vector, is used as the vector, a λ phage-based cDNA library can be constructed by in vitro packaging.

It is also possible to use, as said cDNA library, commercially available cDNA libraries, for example various cDNA libraries available from Clontech.

In a preferred embodiment of the invention, a cDNA library is prepared using λgt11 as the vector and lysogenic bacterial colonies are immobilized, by a conventional method, on a nitrocellulose filter saturated with an inducer such as IPTG.

Cells immobilized on the nitrocellulose filter are grown until sufficient extracellular secretion of the nuclear factor resulting from expression of the gene according to the invention. When *E. coli* Y1090, which is used in the examples to be described later herein, is used as the host, cells are generally grown at 42° C. for 3 to 4 hours and then lysogenization is caused by overnight incubation at 37° C. The nuclear factor produced is immobilized on the nitrocellulose for use in the subsequence screening.

The base sequence SEQ ID NO:2, to which the nuclear factor resulting from expression of the gene according to the invention specifically binds, is labeled, for example with $^{32}P$, and allowd to bind to the nuclear factor on the nitrocellulose filter spotted therewith, followed by autoradiography for identifying radioactive spots. The λ phages corresponding to the spots are lysed from the gel and transfected to the host cells, for example *E. coli* Y1090, thereafter the same procedure is repeated to isolate desired clones.

A DNA containing the gene according to the invention can be prepared from an appropriate one of the isolates by a conventional method (cf. Maniatis, T., Fritsch, E. F. and Sambrook, J.: Molecular Cloning—A Laboratory Manual, Cold Spring Harbor Laboratory, 1982).

The gene obtained in the above manner, when digested with an appropriate restriction enzyme or enzymes, gives an appropriate restriction fragment of DNA.

A recombinant plasmid can be produced by inserting the above-mentioned fragment into an appropriate plasmid vector, for example pUC18 [Yanisch-Perron, C., Vieira, J. and Messing, J., Gene, 33, 103–119 (1985)], using a restriction enzyme or enzymes and ligase.

The thus-obtained recombinant plasmid can be used to transform an appropriate host, for example *Escherichia coli*, and, using the thus-obtained transformants, the restriction enzyme map of each clone in which said gene is encoded can be drawn, for example, by the method described in Maniatis, T., Fritsch, E. F. and Sambrook, J.: Molecular Cloning—A Laboratory Manual, Cold Spring Harbor Laboratory, 1982, pages 104–106.

The base sequence of the clone mentioned above can be determined by a conventional method, for example by the dideoxy method of Sanger et al. [Sanger, F., Nicklen, S. and Coulson, A. E.: DNA sequencing with chain-terminating inhibitors, Proc. Natl. Acad. Sci. U.S.A., 74, 5463–5467 (1977)].

In this way the whole DNA sequence of the C/EBP2 gene obtained in the above manner can be determined.

It can be confirmed, by a conventional method, for example the footprinting method or the gel shift assay [Aguilera, R. J. et al., Cell, 51, 909–917 (1987)], that the gene according to the invention codes for NF-IL6 reported at the Annual Meeting of the Japanese Society for Immunology for 1988.

The procedure for confirmation by the footprinting method may be as follows.

A clone containing the gene according to the invention as isolated in the above manner is incorporated into an appropriate host, for example *E. coli* Y1089, and a transformant appropriately selected is cultured at 37° C. for about 1 hour in a medium containing isopropyl β-D-thiogalactopyranoside (IPTG) (Sigma) for inducing the expression of the gene according to the invention. Thereafter, cells are subjected to repeated freeze-thaw cycles to give a cell extract. As a control, a cell disruption product is prepared without stimulation with IPTG. The level of addition of IPTG is preferably about 10 mM.

The c-fos basal enhancer region [−179 to −111 bp region of the human IL-6 gene; Isshiki, H. et. al., Mol. Cell. Biol., 10, 2757–2764 (1990)], which contains the 14 bp palindrome to which the nuclear factor encoded by the gene according to the invention specifically binds, is terminally labeled and partially methylated with dimethyl sulfate and then mixed with the cell extract mentioned above. The mixture is subjected to electrophoresis in the same manner as in gel shift assay. The free band without protein binding and a band slower in migration are recovered, both reacted with piperidine and then allowed to migrate on a sequence gel. In this way the protein-bound base can be identified.

The procedure for confirmation by the gel shift assay is as follows.

Fragments of the amino acid sequence of the DNA-binding domain as deduced from the base sequence of the C/EBP2 gene, which is found to be representable by the formula (1) shown later herein, are chemically synthesized and polyclonal antibodies are produced by a conventional method using said fragments as antigens.

A polypeptide domain corresponding to the gene portion rich in basic amino acid codons and showing homology to that gene portion which codes for an amino acid sequence binding to the DNA for C/EBP [Landschulz, W. H. et al., Genes Dev., 2, 786–800 (1988); Landschulz, W. H. et al., Science, 240, 1759–1764 (1988)] was estimated to be the DNA-binding site.

When the site of recognition by said polyclonal antibodies is in agreement with the DNA-binding site of C/EBP2, C/EBP2 cannot bind to the DNA-binding site in gel shift assay and the band slow in migration cannot be formed.

The molecular weight of C/EBP2 can be determined by allowing $^{35}$S-labeled methionine to be taken up by glioblastoma cells, reacting the thus-prepared $^{35}$S-labeled C/EBP2 in the form of a nuclear factor extract with the polyclonal antibodies mentioned above and subjecting the labeled complex resulting from the antigen-antibody reaction to SDS-PAGE.

The molecular weight (MW) of C/EBP2 as determined in the above manner under reducing conditions is about 38,000. This value is substantially in agreement with the molecular weight of the polypeptide deduced from the base sequence of SEQ ID NO:1 shown below. By this the identity of the extracted product of expression of the gene according to the invention with C/EBP2 can be confirmed.

The whole DNA base sequence of the C/EBP2 gene as found in the above manner is as shown by SEQ ID NO:1.

The gene according to the invention can also be isolated directly from the clone containing the gene of the invention as isolated in the same manner as above.

The gene according to the invention can also be prepared by a usual process for the chemical synthesis of nucleic acids, for example the phosphite triester process [Nature, 310, 105 (1984)], based on the base sequence SEQ ID NO:1.

The gene according to the invention as determined and produced in the above manner has the following characteristic features:

i) It codes for 345 amino acid residues.
ii) The expression product has a leucine zipper structure on the C terminal side.
iii) The expression product has a basic amino acid rich domain on the N terminal side of the leucine zipper structure.
iv) The expression product has a domain rich in Ser and a domain rich in Pro in the N terminus.
v) The expression product shows 81% homology with C/EBP.

Thus, C/EBP2, namely the product of expression of the gene according to the invention, can be produced and recovered in an easy and simple manner and in large quantities by recombinant DNA techniques using the gene of the invention which can be obtained as above.

While it is essential to use the above-specified gene (DNA) of the invention in this process for preparing the recombinant C/EBP2 resulting from expression of the gene, said recombinant C/EBP2 can be produced basically by using various genetic engineering techniques (cf. e.g. Science, 224, 1431 (1984); Biochem. Biophys. Res. Comm., 130, 692 (1985); Proc. Natl. Acad. Sci. U.S.A., 80, 5990 (1983); Laid-open European Patent Specification No.187991; Maniatis, T. et al., Molecular Cloning, Cold Spring Harbor Laboratory, 1982].

More specifically, the recombinant C/EBP2 can be produced by preparing a recombinant DNA which allow expression of the gene according to the invention in host cells, introducing the DNA into the host cells for transformation thereof and cultivating an appropriate transformant thus obtained.

Useful host cells can be either eukaryotic or prokaryotic cells. The eukaryotic cells include cells of vertebrate animals, yeasts, etc. Generally used as cells of vertebrate animals are, for example, Jurkat cells, COS cells which are simian cells [Gluzman, Y., Cell, 23, 175–182 (1981)], dihydrofolate reductase deficient Chinese hamster ovary cells [Urlaub, G. and Chasin, L. A., Proc. Natl. Acad. Sci. U.S.A., 77, 4216–4220 (1980)], etc., while useful cells are not limited to these cells. Useful expression vectors for vertebrate cells are those generally having a promoter located upstream from the gene to be expressed, RNA splicing sites, a polyadenylation site, a transcription termination sequence, etc. These vectors may further have a replication origin when required. A preferred expression vector is, but is not limited to, CMVNF-IL6 which contains the CMV promoter, which is a cytomegalovirus-derived promoter, as located upstream from the gene according to the invention.

Yeasts are widely used as eukaryotic microorganisms, among which those of the genus Saccharomyces can be advantageously used. Examples of the expression vector for use in yeasts and like eukaryotic microorganisms include pAM82 (Miyanohara, A. et al., Proc. Natl. Acad. Sci. U.S.A., 80, 1–5 (1983)] having a promoter for the acid phosphatase gene, etc.

E. coli and Bacillus subtilis are generally used as prokaryotic hosts. In an embodiment of the invention where one of such prokaryotic hosts is used as the host, it is preferable that a plasmid vector capable of replication in said host be used and an expression vector be prepared by inserting into said plasmid vector the gene according to the invention together with a promoter, an SD (Shine-Dalgarno) sequence and further an initiation codon (e.g. ATG) necessary for initiating protein synthesis as located upstream from said gene so that said gene can be expressed. Escherichia coli K12, for instance, is a strain widely used as the host, while pBR322 is generally used as the vector. However, these are not limitative, and various other known strains and vectors are usable. Examples of promoters usable are tryptophan (trp) promoter, lpp promoter, $P_L$ promoter, lac promoter, etc. The gene can be expressed by using any of these promoters.

A preferred method of producing the recombinant C/EBP2 using the gene according to the invention uses, as the host cells, Jurkat cells (a T cell line) [Taniguchi, T. et al., Nature, 302, 305–310 (1983)], for instance. An expression vector which can be used in said method has a transcriptional promoter, transcription termination signal, RNA splicing sites, etc. As an example thereof, there may be mentioned CMV-C/EBP2, which is to be described later herein in an example. In this case, the desired expression vector can be prepared by inserting the gene according to the invention into the vector at the restriction enzyme HindIII site located downstream from the CMV early gene promoter.

The thus-obtained desired recombinant DNA can be introduced into host cells for transformation or transfection thereof by any of various methods in general use. For example, the expression vector with the desired gene inserted in the above-mentioned vector CMV-C/EBP2 can be caused to be taken up by Jurkat cells by the DEAE-dextran method or calcium phosphate-DNA coprecipitation method, whereby desired transformant cells can be readily obtained.

Another preferred method of producing the recombinant C/EBP2, which is the product of expression of the gene according to the invention, by using the gene uses dihydrofolate reductase deficient Chinese hamster ovary cells, for instance, as the host cells.

A further method of producing the desired recombinant C/EBP2 by using the gene according to the invention uses prokaryotic cells, such as E. coli cells, as the host cells and causes the desired protein to be accumulated in the cells or to be secreted extracellularly through the intermediary of a signal peptide. Examples of useful signal peptides are various known ones including, for example, Lpp, OmpA, OmpF, PhoE and like outer membrane proteins, and PhoA, Bla, PstS and like periplasm proteins.

The desired transformant thus obtained can be clutivated by a usual method, whereby the recombinant C/EBP2 is produced and accumulated. The medium to be used for the cultivation can suitably be selected from among those usually used for the host cell employed. For instance, when a transformant derived from an E. coli strain employed as the host is cultivated, the cultivation can be carried out in such a medium as LB medium, E medium, M9 medium, M63 medium or the like. Various carbon sources, nitrogen sources, inorganic salts, vitamins, natural extracts, physiologically active substances, etc. which are generally known can be added to these media when required. Transformant cells derived from Jurkat cells employed as host cells can be cultivated in RPMI-1640 medium, Dulbecco's modified Eagle's MEM, etc. which may be supplemented with fetal calf serum (FCS) or like serum component when so required.

Transformant cultivation can be performed under conditions. suitable for the growth of host cells. In the case of E. coli, for instance, cultivation can be carried out at a pH of about 5 to about 8, preferably about 7, and at a temperature of about 20° to about 43° C., preferably about 37° C.

In the above manner, the desired recombinant C/EBP2 is produced and accumulated in transformant cells or secreted extracellularly. Said C/EBP2 can be isolated and purified by various separation procedures utilizing the physical or chemical properties of the product. [See, for example, "Biological Data Book II," pp. 1175–1259 1st edition, 1st printing, June 23, 1980, published by Kabushiki Kaisha Tokyo Kagakudojin; Biochemistry, 25 (25), 8274–8277 (1986); Eur. J. Biochem., 163, 313–321 (1987)]. Examples of useful procedures are reconstruction treatment, treatment with a protein precipitating agent (salting out), centrifugation, osmotic shock method, ultrasonication, ultrafiltration, molecular sieve chromatography (gel filtration), adsorption chromatography, ion-exchange chromatography, affinity chromatography, high-performance liquid chromatography (HPLC) and like liquid chromatography, dialysis, and combinations of such procedures.

In the above manner, the desired recombinant C/EBP2 can be produced on a commercial scale in an easy and simple manner and in high yield and high purity.

For use as a drug, the C/EBP2 obtained in the above manner should preferably have a dosage form enabling it to be directly taken up by cell nuclei. More specifically, it should preferably be used in the form of a liposome preparation designed, by adequately modifying the surface of said preparation, such that the C/EBP2 can be directly taken up by cell nuclei.

In accordance with the invention, a gene for C/EBP2 is provided. Genetic engineering techniques make it possible to product C/EBP2 using said gene. Thus the invention also provides the recombinant C/EBP2 thus expressed. Said recombinant C/EBP2 is useful as a hematopoiesis enhancer.

The following reference examples and working examples are further illustrative of the invention.

REFERENCE EXAMPLE 1

1. Preparation of a Synthetic Probe

Oligonucleotides SEQ ID NO:3 and SEQ ID NO:4 were synthesized using a DNA synthesizer.

Thus, the completely protected DNAs were synthesized using an automatic synthesizer (model 380A DNA synthesizer, Applied Biosystems Inc., Foster City, Calif., 94404, U.S.A.) by the solid-phase phosphite triester method [Nature, 310, 105 (1984)] in which N,N-dialkylmethylphosphoroamidite derivatives were used as condensation units. The completely protected DNAs were then treated with 28% aqueous ammonia at 55° C. for 10 hours, whereby the protective groups (acyl groups on the amino groups of A, G and C) other than the DMTr (dimethoxytrityl) attached to the OH at the 5' terminus and serving as a protective group were eliminated to give partially protected DNAs (DMTr derivatives). The DMTr derivatives were purified by reversed-phase HPLC using $C_{18}$ as a carrier and then treated with 80% acetic acid at room temperature for 10 minutes for removing the DMTr group mentioned above. The bases obtained were purified by electrophoresis on a 10% polyacrylamide gel containing 7M urea and further with Biogel P-30 (Bio-Rad) to give the desired oligonucleotides (each 32-met).

The thus-obtained oligonucleotides were phosphorylated at the 5' terminus using T4 polynucleotide kinase and then annealed and ligation was performed for 1 hour using a ligation kit (Takara Shuzo). The ligation product was further ligated to pUC18 cleaved in advance with the restriction enzyme BamHI. The ligation mixture was used to transform E. coli JM109. The plasmid DNA was recovered from each transformant obtained and examined for insert size by polyacrylamide gel electrophoresis. A clone containing four repetitions of the above-mentioned oligonucleotide unit was selected. The probe used was prepared by cleaving the plasmid DNA with the restriction enzymes XbaI and EcoRI, labeling the resultant fragments by cohesive end-to-blunt end conversion using $\alpha$-$^{32}$P-dCTP and DNA polymerase I Klenow fragment and subjecting the conversion reaction mixture to polyacrylamide gel electrophoresis, followed by elution of the desired $^{32}$P-labeled DNA fragment.

EXAMPLE 1

Determination of the Base Sequence of the Nuclear Factor According to the Invention The base sequence of the nuclear factor according to the invention (C/EBP2) was determined by the method of Singh et al. [Singh, H. et al., Cell, 52, 415–423 (Feb. 12, 1988)] using the λgt11 library (human peripheral blood monocyte cDNA) obtained from Clontech.

Thus, E. coli Y1090 was sowed onto LB medium containing 50 µg/ml of ampicillin and cultured at 37° C. One of the resultant colonies was picked up and grown in LB medium containing 0.2% maltose at 37° C. under aerobic conditions until a state of saturation was arrived at. Thereafter, 0.2 ml of the Y1090 culture was mixed with 0.1 ml of a λgt11 phage dilution (concentration: $5 \times 10^4$), incubation was carried out at 37° C. for 15 minutes, and the culture was sowed onto the LB plate, 15 cm in diameter, together with 7.0 ml of soft agar.

After 3.5 hours of incubation at 42° C., a nitrocellulose filter saturated with 10 mM IPTG in advance was placed on the plate, and incubation was conducted overnight at 37° C.

After the above incubation and the subsequent standing at 4° C. (15 minutes), the filter was removed from the plate and pretreated with TNE-50 (5% nonfat milk powder, 50 mM Tris, pH 6.5, 1 mM EDTA, 1 mM DTT) at 4° C. for 1 hour.

Then the $^{32}$P-labeled probe prepared in the reference example 1 given above was added and incubation was performed at room temperature for 1 hour. The filter was washed by gently shaking with TNE-50 for 30 minutes. This washing procedure was repeated three times in all. After washing, the filter was air-dried and probe-bound colonies were identified by autoradiography.

The colonies so identified were isolated and the same procedure was repeated three times.

As a result, a C/EBP2-producing strain was isolated from among $5 \times 10^5$ plaques. This strain was named E. coli Y1090/IS3.

The strain obtained as described above, namely E. coli Y1090/IS3 was grown and then an IS3-encoding recombinant phage DNA (IS3 DNA) was prepared by the method described in Maniatis, T., Fritsch, E. F. and Sambrook, J.: Molecular Cloning—A Laboratory Manual, Cold Spring Harbor Laboratory, 1982.

The IS3 DNA was digested with the restriction enzyme EcoRI (Takara Shuzo) and a DNA fragment of about 700 base pairs was isolated.

Separately, the plasmid vector pUC18 (Takara Shuzo) was digested with the same restriction enzyme EcoRI and the 700-base-pair insert derived from the IS3 DNA was ligated to the cleaved vector using T4 DNA ligase (Takara Shuzo) to give a recombinant plasmid coding for IS3, namely pIS3.

The thus-obtained recombinant plasmid pIS3 was introduced into competent cells of E. coli JM83 for transduction thereof.

The above-mentioned pIS3 was treated by the procedure described in Maniatis, T., Fritsch, E. F. and Sambrook, J.: Molecular Cloning—A Laboratory Manual, Cold Spring Harbor Laboratory, 1982, pages 104–106 and further the restriction enzyme map of the pIS3 clone coding for IS3 was prepared by the method described in the reference cited above on pages 150–163.

The results are shown in FIG. 1.

Said figure indicates that the Sac, Spl, Sac, Pst and Sac cleavage sites are located in IS3 in that order.

Determination of the Base Sequence of the pIS3 Clone]

The base sequence of the pIS3 clone was determined by the method of Sanger et al. [Sanger, F., Nicklen, S. and Coulson, A. R.: DNA sequencing with chain-terminating inhibitors, Proc. Natl. Acad. Sci. U.S.A., 74, 5463–5467 (1977)].

For further determination of the base sequence of the remaining portions of the gene coding for C/EBP2, the following procedure was followed.

Thus, a cDNA clone coding for C/EBP2 was isolated using, as a probe, the 700-bp IS3 gene obtained as above and the whole sequence thereof was determined.

A human peripheral monocyte cDNA library and a human placental cDNA library (Clontech) were used. As mentioned hereinbefore, these phages and E. coli Y1090 were sowed onto LB plates and grown. After overnight standing at 37° C. for plaque formation, clones showing homology to IS3 were isolated by the plaque hybridization method [cf. Benton, W. D. and Davis, R. W., Science, 196, 180 (1977)]. The clones so isolated were shown in FIG. 1 as HP1, HP2 and HM1, respectively. Joining them together gave a full-length cDNA. This had the DNA sequence of SEQ ID NO:1 shown hereinbefore.

Screening out of the Genomic Gene According to the Invention Using a Genomic Library A human placenta-derived EMBL3 genomic library (Clontech) was used for screening out the gene according to the invention.

Thus, E. coli NM538 [Frischhauf, A. M. et al., J. Mol. Biol., 170, 827 (1983)] was mixed with the EMBL3 recombinant phages with the genomic DNA integrated therein, the mixture was sowed onto an LB plate and grown for plaque formation, and the genomic gene according to the invention was screened out by the above-mentioned plaque hybridization method. The probe used was the above-mentioned IS3 gene labeled with $^{32}$P.

As a result, a strain, E. coli NM538/G16, containing a gene homologous to the IS3 gene was obtained.

With this strain, the gene map and gene sequence of the C/EBP2 genomic gene G16 were determined by the methods of Maniatis (Maniatis, T., Fritsch, E. F. and Sambrook, J.: Molecular Cloning—A Laboratory Manual, Cold Spring Harbor Laboratory, 1982).

It was found that the sequence which the G16 gene has covers the whole sequence of the C/EBP2 gene shown by SEQ ID NO:1.

Expression of the Gene According to the Invention in Jurkat Cells (1) Construction of K9CAT and IL-1RE-K9CAT These plasmids were constructed as described in Mol. Cell. Biol., 10, 2757–2764 (1990).

Thus, from pGEM-B672A [Yasukawa, K. et al., EMBO J., 6, 2939–2945 (1987)] subcloned from an IL-6 genomic clone into the pGEM vector, the IL-6 promoter region was excised using the restriction enzymes BamHI and XhoI. Said promoter region was inserted into the plasmid pUC18 between the BamHI and SalI sites thereof. The resultant plasmid was cleaved with BamHI and SacI, followed by successive deletion from the BamHI side using a deletion kit for kilo-sequencing (Takara Shuzo) to give several deletion mutants. From among them, Δ122 having the −122 to +12 region of the IL-6 genomic gene was selected for constructing K9CAT. Thus, the Δ122 region (−122/+12) was inserted into pSVOCAT at the HindIII site to give K9CAT.

Separately, a sequence of 3 copies of the 14 bp palindrome (SEQ ID NO:5) was prepared and the sequence was joined to the upstream side of the −122/+12 region of the above-mentioned Δ122 followed by insertion of the joining product into pSVOCAT at the HindIII site thereof gave IL-1RE-K9CAT.

(2) Construction of CMV-NFIL6(+) and CMV-NFIL6(−)

From the above E. coli NM538/G16 (the genomic clone G16 containing the C/EBP2 gene), a C/EBP2 gene-containing DNA fragment was subcloned into the plasmid pUC18 between the BamHI and EcoRI sites thereof using BamHI and EcoRI. Using the deletion kit for kilo-sequencing (Takara Shuzo), deletion was caused to take place from the BamHI site until shortening was effected to 102 bp upstream from ATG for C/EBP2 to give pUC-C/EBP2del 5.

A PstI-EcoRI DNA fragment (Pst$^J$ being located in the coding region for C/EBP2 and EcoRI downstream therefrom) was excised from pUC-C/EBP2del 5 and a PstI-EcoRI DNA fragment (EcoRI being a linker site for λ phage) of the cDNA clone HP2 was inserted in place of the excised DNA fragment. The EcoRI site of the thus-obtained plasmid was converted to a BamHI site and the deletion site thereof to a HindIII site, using appropriate linkers. Then, the C/EBP2 gene-containing BamHI-HindIII DNA fragment excised from the site conversion product was inserted into the plasmid CMV-CAT in place of the CAT gene region removed by cleavage with HindIII and BamHI, to give CMV-NFIL6(+).

On the other hand, CMV-NFIL6(−) was prepared in the same manner as above except that, prior to insertion into the plasmid CMV-CAT between the HindIII and BamHI sites thereof, the EcoRI site was converted to a HindIII site and the deletion site to a BamHI site, using appropriate linkers.

For confirming intracellular expression of the gene according to the invention, the transfection method using DEAE-dextran (DNA Cloning, Vol. II, edited by D. M. Glover, pages 154–155, IRL Press, Oxford, 1985) was used.

T cell line Jurkat cells [Taniguchi, T. et al., Nature, 302, 305–310 (1983)] were used and transfected in the following manner. Northern blot analysis using C/EBP2 as a probe revealed that the C/EBP2 gene is not expressed in Jurkat cells as such.

Thus, $10^7$ Jurkat cells were incubated at 37° C. for 1 hour in 1 ml of DMEM containing 250 μg/ml of DEAE-dextran plus DNA (expression vector 5 μg + reporter 5 μg), then washed with DMEM, incubated further in 10% FCS plus DMEM for 40 hours, and assayed for CAT activity by the method described in the literature [Gorman, C. M. et al., Mol. Cell. Biol., 2. 1044–1051 (1982)].

The following four groups of experiments were conducted.

|  | IL-1RE-K9CAT | CMV-NFIL6 (+) | CMV-NFIL6 (−) |
|---|---|---|---|
| Group I | 5 µg | — | — |
| Group II | 5 µg | 5 µg | — |
| Group III | — | — | 5 µg |
| Group IV | — | — | — |

As a result, spots appeared only in Group II which were not observed in other groups, proving that C/EBP2 expressed in Jurkat cells did act on the IL-1RE-K9CAT gene simultaneously used for transfection to thereby cause expression of the CAT gene located downstream from the IL-6 gene.

EXAMPLE 2

Confirmation of the Identity of the Product of Expression of the Gene According to the Invention with C/EBP2 by Gel Shift Assay and Methylation Interference Assay (1) Extraction of the Product of Expression of the Gene According to the Invention 1) Production of a Recombinant Having the Gene According to the Invention The IS3 gene-containing clone obtained in Example 1 was incorporated into the host E. coli Y1089 to give a recombinant.

Thus, E. coli Y1089 was sowed onto LB medium containing 50 µg/ml of ampicillin and cultured at 37° C. The resultant colonies were picked up one by one and each was sowed onto LB medium containing 0.2% maltose and grown at 37° C. under aerobic conditions until a state of saturation. Then, 0.1 ml of the IS3 gene-containing clone (λgtll phage) was added to 0.2 ml of the Y1089 culture, and the mixture was incubated at 37° C. for 15 minutes for causing absorption of the phage by E. coli Y1089.

Then, lysogenic colonies of E. coli Y1089 capable of growing at 32° C. but incapable of growing at 42° C. were screened out. In this way, an IS3 gene recombinant was obtained.

The strain obtained was named E. coli Y1089/IS3.

2) Extraction of the IS3 Gene Expression Product

The recombinant obtained above in 1), namely E. coli Y1089/IS3, was precultured in LB maltose medium at 37° C. for 24 hours. Subculture was performed from the preculture to LB maltose medium containing 10 mM IPTG, followed by incubating at 37° C. for 1 hour.

After incubation, cells were harvested and subjected to repeated freeze-thaw cycles. The thus-obtained cell extract was used as the IS3 gene expression product.

(2) Extraction of C/EBP2

SK-MG-4 glioblastoma cells [Yasukawa, K. et al., EMBO J., 6, 2939–2945 (1987)] were grown in DMEM containing 10% FCS at 37° C. SK-MG-4 cells stimulated with IL-1 (Otsuka Pharmaceutical) (100 U/ml, 6 hours), and unstimulated SK-MG-4 cells were respectively collected. The cell membrane was disrupted to render nuclei naked and then the cell homogenate was centrifuged (4° C., 2,000 rpm, 10 minutes) to give a sediment, namely a cell nucleus fraction.

This cell nucleus fraction was extracted with 0.4M NaCl and further centrifuged (4° C., 4,000 rpm, 30 minutes) to give a supernatant.

Said supernatant was used as the C/EBP2 extract.

(3) Collection of the $^{32}$P-Labeled IL-6 Promoter (−179 to −111)

1) Production of the IL-6 Promoter (−179/−111)

The plasmid pGEM-B672A [Yasukawa, K. et al., EMBO J., 6, 2939–2945 (1987)] containing the 5' upstream region of the human IL-6 gene was subjected to successive deletion from the 5' upstream BamHI site using the deletion kit for kilo-sequencing (Takara Shuzo) to give various deletion mutants.

From among these deletion mutants, the mutant having the region from the IL-6 transcription initiation site up to the point 180 bp upstream therefrom was selected and treated with HaeIII acting on the HaeIII restriction site located at the −111 bp point of said mutant, to give the IL-6 promoter (−179/−111).

Said promoter fragment was inserted into pUC18 between the BamHI and SmaI sites.

The plasmid resulting from insertion of the IL-6 promoter (−179/−111) into the pUC18 vector was digested with XbaI and EcoRI and a fragment was isolated.

Said fragment was terminally labeled using $^{32}$P-labeled dCTP and the labeled fragment was used as a DNA probe. The terminal labeling was performed by a usual method (Maniatis, T., Fritsch, E. F. and Sambrook, J.: Molecular Cloning—A Laboratory Manual, Cold Spring Harbor Laboratory, page 115, 1982) using Klenow fragment.

(4) Confirmation of the Identity of the Product of Expression of the Gene According to the Invention with C/EBP2 by Gel Shift Assay Based on the amino acid sequence deduced from the base sequence specified hereinbefore, the domains supposedly binding to DNA, namely a protein of SEQ ID NO:31 (antigen I) corresponding to the base sequence SEQ ID NO:6 and a protein of SEQ ID NO:32 (antigen II) corresponding to the base sequence SEQ ID NO:7 were chemically synthesized (using an Applied Biosystems model 430A peptide synthesizer) and polyclonal antibodies were prepared using these synthetic peptides as antigens.

Thus, female New Zealand rabbits weighing 2.5 to 3.0 kg were multiply immunized intracutaneously with 100 µg per animal of one of the above-mentioned synthetic peptides together with an equal volume of complete Freund adjuvant and thereafter immunized with 100 µg of the same synthetic peptide combined with incomplete Freund adjuvant at intervals of 2 weeks (four immunizations inclusive of the first one). One week after completion of the immunization, the rabbits were exsanguinated and polyclonal antibodies were obtained.

The polyclonal antibody to the antigen I is hereinafter referred to as "antibody I" and the polyclonal antibody to the antigen II as "antibody II".

The unstimulated glioblastoma cell-derived crude C/EBP2 extract (4 µg) and the IL-1-stimulated glioblastoma cell-derived crude C/EBP2-extract (4 µg) each obtained in Example 2-(2) were respectively reacted with 6 µg of the antibody I or II at 37° C. for 2 hours.

A 4-µg portion of each reaction mixture and 4 µg of the corresponding crude C/EBP2 extract before reaction with the polyclonal antibody were respectively reacted with 3 picomoles of the $^{32}$P-labeled IL-6 promoter (−179/−111) obtained in Example 2-(3)-1) at 4° C. for 0.5 hour in gel shift buffer [10 mM HEPES (pH 7.9), 50 mM NaCl, 5 mM Tris-HCl (pH 7.0), 1 mM dithiothreitol, 15 mM EDTA and 10% glycerol]. To each reaction mixture was added 5 μl of a dye solution for electrophoresis (5% glycerol, 50 mM EDTA, 0.05% bromophenol blue and 0.05% xylene cyanol). The mixture was subjected to polyacrylamide gel (5%) electrophoresis, followed by autoradiography of the gel.

When the glioblastoma cell-derived C/EBP2 as such was reacted with the labeled IL-6 promoter, the binding reaction between C/EBP2 and the [$^{32}$P]-IL-6 promoter (−179/−111) took place, giving a single band in the case of no stimulation and two bands in the case of IL-1 stimulation.

On the other hand, when C/EBP2 was reacted first with the polyclonal antibody I or II mentioned above and then with the [$^{32}$P]-IL-6 promoter (−179/−111), the use of the polyclonal antibody I gave a band slower in migration while the use of the polyclonal antibody II blocked the formation of such band.

These results suggest that the product of expression of the gene according to the invention is identical with C/EBP2.

(5) Confirmation of the Identity of the Product of Expression of the Gene According to the Invention with C/EBP2 by Methylation Interference Assay After conducting gel shift assay following the procedure of Example 2-(4), the bound DNA probe and free DNA probe were extracted from the gel using a DNA probe prepared by $^{32}$P labeling and methylation of the IL-6 promoter (−179/−111) obtained as described above in (3)-2).

To the extracted DNA probe was added 100 μl of 1M piperidine for cleaving the DNA probe at the methylated base G, followed by analysis by autoradiography on a 10% sequencing gel.

As a result, it was found that C/EBP2 in the Y108-9/IS3 extract gives the same pattern as that shown by C/EBP2 in SK-MG-4.

EXAMPLE 3

Expression of C/EBP2 in E. coli (1) Construction of ptrpΔRBS

The expression vector pTM1 [Imamoro, F., Taisha, 22, 81 (1985)] having a tryptophan promoter and operator sequence was cleaved with the restriction enzymes PstI and BamHI and a DNA fragment (I) (about 1.5 kb) containing the tryptophan promoter and operator was isolated.

Separately, the plasmid pAT153 [Twigg, A. J. and Sherratt, D., Nature, 283, 216 (1980)] was cleaved with the restriction enzymes PstI and BamHI and a DNA fragment (II), about 2.6 kb in size, was isolated. The thus-obtained DNA fragment (I) and DNA fragment (II) were ligated to each other using T4 DNA ligase to give a plasmid, pNS1.

The plasmid pNS1 was cleaved with the restriction enzymes HpaI and ClaI and a DNA fragment (III) resulting from deletion of 32 bp between the HpaI and ClaI sites was isolated. The HpaI and ClaI sites were linked to each other with the oligonucleotides SEQ ID NO:28 and SEQ ID NO:29 using T4 DNA ligase to give ptrpΔRBS.

Figure 2:
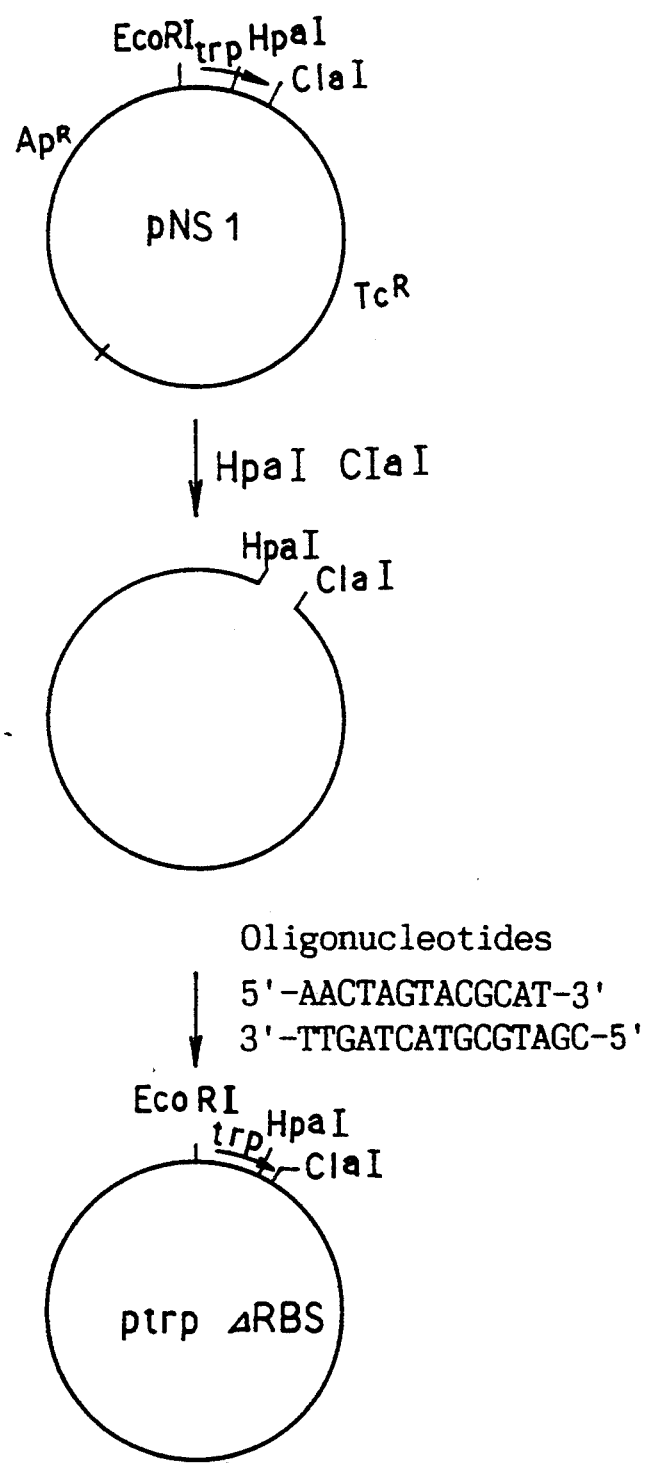
FIG. 2 shows the construction scheme for the plasmid ptrpΔRBS as followed in Example 3 (1).

The construction scheme for this plasmid is shown in FIG. 2.

This is a vector corresponding to pNS1 but missing the region from the second base of the site of transcription initiation due to the tryptophan promoter down to the ClaI recognition site.

(2) Construction of Various Vectors Containing a 5′-Nontranslational Region

Figure 3:
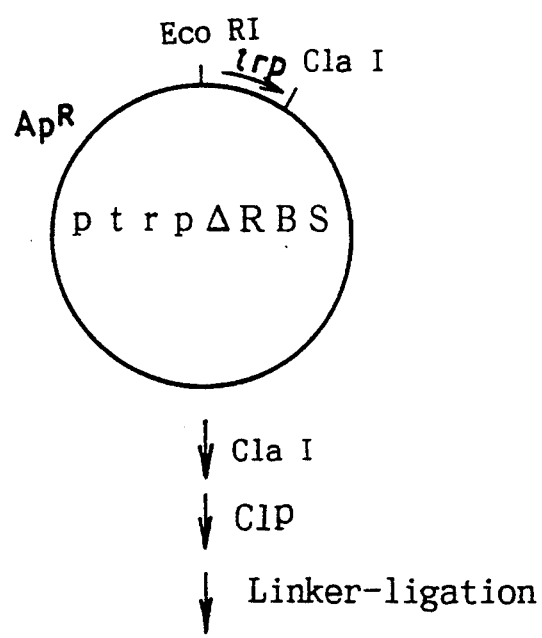
FIG. 3 shows the construction scheme for the plasmid ptrp690 to ptrp699 as followed in Example 3 (2).
Figure 3:
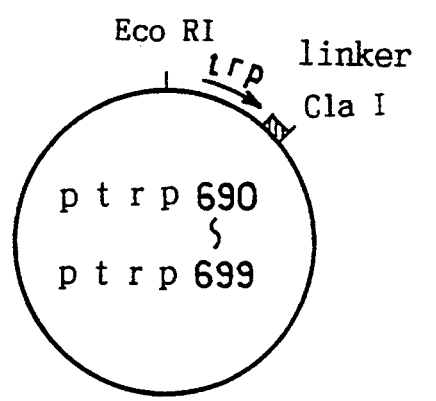

The procedure schematically shown in FIG. 3 was followed as described below.

Thus, the plasmid ptrpΔRBS was cleaved with the restriction enzyme ClaI and then treated with calf intestine alkaline phosphatase to give a DNA fragment (IV) dephosphorylated at the 5′ ends.

Various 5′-nontranslational region-constituting oligonucleotide linkers (shown in FIG. 5 and as follows: ptrp690 as SEQ ID NOS:8 and 9; ptrp691 as SEQ ID NOS:10 and 11; ptrp692 as SEQ ID NOS:12 and 13; ptrp693 as SEQ ID NOS:14 and 15; ptrp694 as SEQ ID NOS:16 and 17; ptrp695 as SEQ ID NOS:18 and 19; ptrp696 as SEQ ID NOS:20 and 21; ptrp697 as SEQ ID NOS:22 and 23; ptrp698 as SEQ ID NOS:24 and 25; ptrp699 as SEQ ID NOS:26 and 27) containing a ribosome binding site were ligated to the DNA fragment (IV) using T4 DNA ligase to give 10 plasmids, ptrp690 to ptrp699.

The thus-obtained plasmids each has under the control of the tryptophan promoter a 5′-nontranslational region containing a ribosome binding site. They have a restriction enzyme ClaI site at the 3′ end of said region. Therefore this ClaI site or the HindIII site located just downstream therefrom can serve as a site for inserting a foreign gene together with a start codon for protein synthesis, whereby a plasmid suited for most efficient expression of a foreign gene can be selected.

(3) Construction of C/EBP2 Expression Vectors

Figure 4:
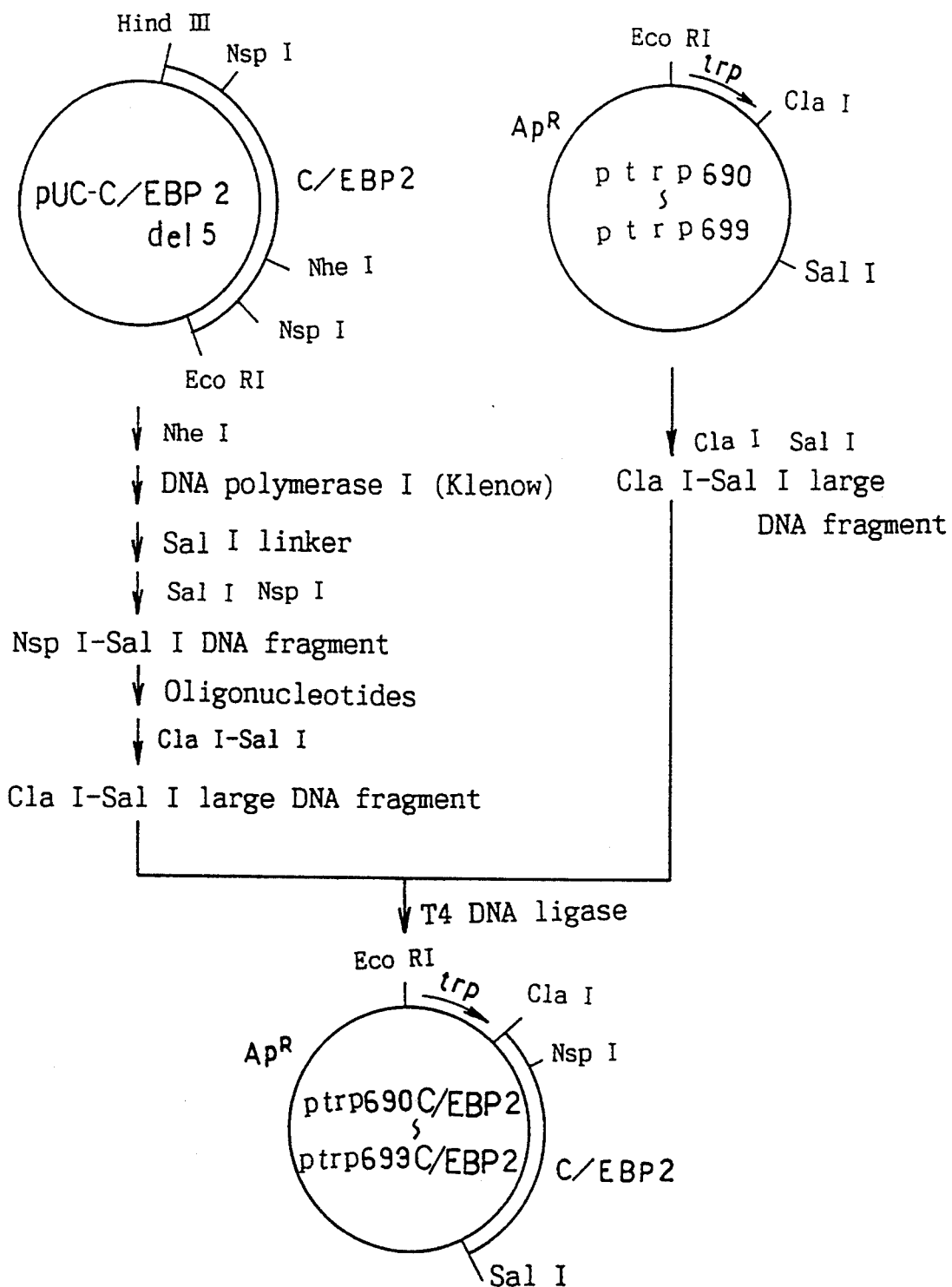
FIG. 4 shows the construction scheme for a C/EBP2 expression plasmid as followed in Example 3 (3).

The procedure schematically shown in FIG. 4 was followed as described below.

The plasmid pUC-C/EBP2del 5 comprising that region of the C/EBP2 gene which covers, in the base sequence of formula (1) given hereinbefore, from the 186the base (joined to HindIII linker) to the 3′ end (joined to an EcoRI linker) was cleaved with the restriction enzyme NheI and then rendered blunt-ended using DNA polymerase I (Klenow fragment). A SalI linker (pGGTCGACC; Takara Shuzo) was ligated to the above blunt-ended DNA using T4 DNA ligase. The reaction product was cleaved with the restriction enzymes SalI and NspI and an NspI-SalI DNA fragment (V) of about 1 kb was isolated.

A pair of oligonucleotides (SEQ ID NO:33 and SEQ ID NO:34) was ligated to the DNA fragment (V) using T4 DNA ligase and the ligation product was cleaved with the restriction enzymes ClaI and SalI to give a claI-salI DNA fragment (VI).

Separately, pNS1 and the plasmids ptrp690 to ptrp699 respectively having various 5′-nontranslational regions were each cleaved with the restriction enzymes ClaI and SalI and respective DNA fragments (VII to XVII), about 3 kb in size, were obtained.

Each of the above-mentioned DNA fragments (VII) to (XVII) was ligated to the DNA fragment (VI) using T4 DNA ligase to give the following C/EBP2 expression plasmids:

| | | |
|---|---|---|
| ptrpC/EBP2, | ptrp690C/EBP2, | ptrp691C/EBP2, |
| ptrp692C/EBP2, | ptrp693C/EBP2, | ptrp694C/EBP2, |
| ptrp695C/EBP2, | ptrp696C/EBP2, | ptrp697C/EBP2, |
| ptrp698C/EBP2 | and ptrp699C/EBP2. | |

(4) Expression of C/EBP2 in *E. coli*

The plasmids obtained as described above in (3) were each used to transform *E. coli* SG21058 [Maurizi, M. R., Trisler, P. and Gottesman, S., J. Bacteriol., 164, 1124 (1985)], which is a lon protease deficient strain. Each transformant obtained was cultured overnight in LB medium [Maniatis, T., Fritsch, E. F. and Sambrook, J.: Molecular Cloning—A Laboratory Manual, page 440, Cold Spring Harbor Laboratory, 1982] containing 100 μg/ml of ampicillin. A 0.5-ml portion of the culture was added to 50 ml of a production medium [M9 medium containing 10 g/liter of Bacto casamino acids (product of Difco), 20 mg/liter of L-cysteine hydrochloride and 10 mg/liter of thiamine hydrochloride, together with 4 g/ml of glucose; cf. the reference cited just above] and shake culture was performed in a 300-ml erlenmeyer flask at 37° C. After 4.5 hours of cultivation, 50 μl of 20 mg/ml 3-β-indoleacrylic acid (Sigma) was added and cultivation was further continued for 4 hours. Then, the C/EBP2 expressed and produced in *E. coli* cells in each culture was analyzed by SDS-polyacrylamide gel electrophoresis (SDS-PAGE).

AS a result, it was found that SG21058 transformants harboring the plasmid ptrp694C/EBP2, ptrp696C/EBP2 or ptrp699C/EBP2 had expressed C/EBP2 in large amounts as evidenced by bands at about 40 KDa.

The SG21058 strain harboring the above-mentioned ptrp699C/EBP2 has been deposited with the Fermentation Research Institute, Agency of Industrial Science and Technology, Tsukuda, Japan under the designation "*Escherichia coli* SG21058/ptrp699C/EBP2 and under the deposit number FERM BP-3103.

We claim:

1. An isolated IL-6 gene expression inducing nuclear factor C/EBP2 protein, obtained by the process comprising:
(1) cultivating a host cell which has been transformed with a plasmid containing an isolated DNA molecule comprising the nucleotide sequence represented by SEQ ID NO. 30 which encodes said C/EBP2 protein, wherein the resulting transformed host cell expresses said C/EBP2 protein; and
(2) isolating the resulting C/EBP2 protein expressed by said transformed host cell.

2. The isolated C/EBP2 protein of claim 1, wherein said transformed host cell is *E. coli* SG21058/ptrp699c/EBP2.

* * * * *